US011020353B2

(12) United States Patent
Kawada et al.

(10) Patent No.: US 11,020,353 B2
(45) Date of Patent: Jun. 1, 2021

(54) FILM COATING COMPOSITION, SOLID ORAL FORMULATION, AND METHOD FOR PRODUCING THE SAME

(71) Applicant: JAPAN VAM & POVAL CO., LTD., Osaka (JP)

(72) Inventors: Shotaro Kawada, Osaka (JP); Masatoshi Kawanishi, Osaka (JP)

(73) Assignee: JAPAN VAM & POVAL CO., LTD., Osaka (JP)

( * ) Notice: Subject to any disclaimer, the term of this patent is extended or adjusted under 35 U.S.C. 154(b) by 0 days.

(21) Appl. No.: 15/523,752

(22) PCT Filed: Sep. 30, 2015

(86) PCT No.: PCT/JP2015/077760
§ 371 (c)(1),
(2) Date: May 2, 2017

(87) PCT Pub. No.: WO2016/072179
PCT Pub. Date: May 12, 2016

(65) Prior Publication Data
US 2017/0348242 A1    Dec. 7, 2017

(30) Foreign Application Priority Data

Nov. 5, 2014  (JP) .............................. JP2014-225026
Apr. 9, 2015  (JP) .............................. JP2015-080261

(51) Int. Cl.
*A61K 9/28*   (2006.01)
*C09D 129/04* (2006.01)
*A61K 47/34*  (2017.01)
*A61K 9/00*   (2006.01)

(52) U.S. Cl.
CPC ............ *A61K 9/284* (2013.01); *A61K 9/0056* (2013.01); *A61K 47/34* (2013.01); *C09D 129/04* (2013.01)

(58) Field of Classification Search
None
See application file for complete search history.

(56) References Cited

U.S. PATENT DOCUMENTS

| | | | | |
|---|---|---|---|---|
| 2009/0291282 A1* | 11/2009 | Kitamura | ................... | C08J 5/18 428/220 |
| 2010/0233262 A1* | 9/2010 | Kato | ...................... | A61K 9/284 424/482 |
| 2011/0027362 A1* | 2/2011 | Yanagida | ............. | A61K 9/2018 424/465 |
| 2011/0034418 A1* | 2/2011 | Beltz | ..................... | A61K 9/0024 514/94 |
| 2011/0305756 A1 | 12/2011 | Hayashi et al. | | |
| 2012/0157580 A1 | 6/2012 | Yoshino et al. | | |
| 2013/0230480 A1* | 9/2013 | Saguchi | ................. | A01N 25/18 424/84 |

FOREIGN PATENT DOCUMENTS

| | | | |
|---|---|---|---|
| JP | 56-144705 | 11/1981 | |
| JP | 59-42325 | 3/1984 | |
| JP | 8-59512 | 3/1996 | |
| JP | 2002-105383 | 4/2002 | |
| JP | 2004-26675 | 1/2004 | |
| JP | 2004143197 A * | 5/2004 | |
| JP | 2007-197410 | 8/2007 | |
| JP | 2008-74770 | 4/2008 | |
| JP | 2008-201711 | 9/2008 | |
| JP | 2008201711 A * | 9/2008 | |
| JP | 2011-195672 | 10/2011 | |
| JP | 2013-253030 | 12/2013 | |
| WO | 2010/110018 | 9/2010 | |
| WO | 2011/025035 | 3/2011 | |
| WO | 2014/017507 | 1/2014 | |
| WO | WO-2014063178 A1 * | 5/2014 | ............. A61K 47/34 |

OTHER PUBLICATIONS

English translation of Shotaro Kawada, Masatoshi Kawanishi, "PVA no Kakushu Parameter no Jozai Coating eno Eikyo", The 31st Seizai to Ryushi Sekkei Symposium Koen Yoshishu, Oct. 10, 2014, pp. 62 to 63.
English translation of Masatoshi Kawanishi, Shotaro Kawada, "Iyaku Grade PVA no Shokai", The 30th Seizai to Ryushi Sekkei Symposium Koen Yoshishu, 2013, pp. 38 to 39.
International Search Report dated Nov. 17, 2015 in International Application No. PCT/JP2015/077760.
Shotaro Kawada, Masatoshi Kawanishi, "PVA no Kakushu Parameter no Jozai Coating eno Eikyo", The 31st Seizai to Ryushi Sekkei Symposium Koen Yoshishu, Oct. 10, 2014 (Oct. 10, 2014), pp. 62 to 63.
"Iyaku Grade PVA no Shokai", Masatoshi Kawanishi, Shotaro Kawada, The 30th Seizai to Ryushi Sekkei Symposium Koen Yoshishu, 2013, pp. 38 to 39.
International Preliminary Report on Patentability and Written Opinion of the International Searching Authority dated May 18, 2017 in corresponding International (PCT) Application No. PCT/JP2015/077760.
Pamphlet of Gohensol and its translation, dated Apr. 1, 2014.
Specialty Grades and its translation, dated Nov. 8, 2018.
General Grade and its translation, dated Nov. 8, 2018.
Certified Experimental Results and its translation, dated Oct. 29, 2018.
Office Action, dated Apr. 23, 2019, in corresponding Japanese Patent Application No. 2016-557493, with English Language translation.
Submission of Publication dated Dec. 25, 2021 as a Third Party Observation in corresponding Japanese Divisional application No. JP 2019-135928, with English-language translation (Continued)

*Primary Examiner* — Susan T Tran
(74) *Attorney, Agent, or Firm* — Wenderoth, Lind & Ponack, L.L.P.

(57) ABSTRACT

Provided are a film coating composition containing a PVA having a degree of hydrolysis of 85.0 to 89.0 mol %, characterized in that even when the composition is used for coating of tablets without any additives other than PVAs, the tablets do not tend to stick to each other; a solid oral formulation using the composition; and a method for producing the same.

9 Claims, 1 Drawing Sheet

(56) References Cited

OTHER PUBLICATIONS

Notice of Reasons for Refusal dated Mar. 9, 2021 in corresponding Japanese divisional application No. JP 2019-135928, with English-language translation.
Certified Experimental Results dated Dec. 23, 2020, with English-language translation.
Matsumoto et al., "Separation of saponification degree distribution of vinyl acetate partial saponification", Polymer Chemistry, vol. 18, No. 191, pp. 169-174 (1961), with English-language translation.
Affidavit to submit Additional Experiments against U.S. Appl. No. 15/532,752 dated Dec. 25, 2020, with English-language translation

* cited by examiner

FILM COATING COMPOSITION, SOLID ORAL FORMULATION, AND METHOD FOR PRODUCING THE SAME

TECHNICAL FIELD

The present invention relates to a film coating composition for use in pharmaceutical solid oral formulations, a solid oral formulation using the composition as a coating, and a method for producing the same. Further, the present invention relates to a film coating composition for producing pharmaceutical solid oral formulations that have high gas barrier property and can be produced with high productivity, a solid oral formulation, and the production thereof.

BACKGROUND ART

In the field of pharmaceutical solid oral formulations, film coating and sugar coating are widely used techniques for coating tablets or the like containing a medicinal substance, for the purposes of masking the unpleasant taste of the medicinal substance, blocking oxygen, moistureproofing, improving the product appearance, etc.

Film coating can be carried out in a simpler way and in a shorter time as compared with sugar coating. In addition, since coating thickness can be reduced in film coating, the size of tablets can be reduced, which leads to another advantage of easy taking of the obtained solid oral formulations.

As a base for film coating, various polymers including hydroxypropylmethylcellulose (hereinafter abbreviated as HPMC) are used, and polyvinyl alcohol (hereinafter abbreviated as PVA) has attracted attention in recent years. Since PVA films are excellent in moistureproofing and gas barrier properties, when a solid formulation containing a medicinal substance that has a strong odor, is easily oxidized, or is hygroscopic is coated with a PVA film, the film can exert an effect of improving the preservation stability or masking the odor.

Generally, PVAs marketed for pharmaceutical use or as products of pharmaceutical grade are so-called partially hydrolyzed PVAs, each of which has a degree of hydrolysis of 85.0 to 89.0 mol %. Possible reasons for this are as follows. In the recent spread of globalization of pharmaceutical products, pharmaceutical companies prefer PVAs having a degree of hydrolysis of 85.0 to 89.0 mol % as a raw material PVA in order to receive approval from the trilateral countries of Japan, the US, and Europe because the standards of degree of hydrolysis of PVA in the official specifications of Japan, the US, and Europe overlap in the range of 85.0 to 89.0 mol %. In addition, partially hydrolyzed PVAs are highly soluble in water and therefore are suitable PVAs for use in oral formulations.

However, when used as a coating base, such a commercially available pharmaceutical PVA having a degree of hydrolysis of 85.0 to 89.0 mol % causes a problem of sticking of solid formulations to each other during coating due to the high stickiness of the PVA aqueous solution and a problem of low productivity due to the adhesion of solid formulations to the coater, which prevents high-speed spraying.

As a method for reducing the stickiness of PVA, Patent Literature 1 has disclosed a composition for coating containing a PVA having a degree of hydrolysis of 90 mol % or higher and water. Also, Patent Literature 1 has disclosed a film coating composition containing PVA and water-soluble polyoxyethylene, and in the Examples thereof, exemplary film coating compositions containing partially hydrolyzed PVA and polyethylene glycol are mentioned.

Further, the present inventors have disclosed a method for coating using a film coating composition containing PVA and a cellulose derivative (Patent Literature 3).

By any of these methods, it is possible to reduce the stickiness of PVA, thereby to increase the spraying speed as compared to that in the case of coating using a partially hydrolyzed PVA having a degree of hydrolysis of 85.0 to 89.0 mol % alone, and thereby to shorten the coating time.

CITATION LIST

Patent Literature

Patent literature 1: JP 59-42325 A
Patent literature 2: JP 8-59512 A
Patent literature 3: JP 2013-253030 A However, the PVA of Patent Literature 1 does not satisfy the degree of hydrolysis standard specified in the United States Pharmacopeia (USP) and therefore cannot be used as a raw material of a pharmaceutical product intended for global-scale development. Also, the PVA has a lower water solubility as compared to a PVA having a degree of hydrolysis of 85.0 to 89.0 mol % and therefore cannot be used for rapidly dissolving solid oral formulations.

In the methods described in Patent Literature 2 and Patent Literature 3, polyoxyethylene or a cellulose derivative is contained as a component other than PVA, and therefore the composition cannot be used for coating of solid formulations containing a medicinal substance that can interact therewith. Further, addition of additives other than PVA, such as polyoxyethylene and a cellulose derivative may be a factor in decreasing the intrinsic moistureproofing and gas barrier properties of PVA.

SUMMARY OF INVENTION

Technical Problem

In view of the above-described circumstances, the objective of the present invention is to provide a film coating composition characterized in that a PVA that meets the standards of degree of hydrolysis of PVA in the official specifications of Japan, the US, and Europe, i.e., a PVA having a degree of hydrolysis of 85.0 to 89.0 mol % is used and that even when the composition is used for coating of tablets without addition of any additive other than the PVA, the tablets do not tend to stick to each other during coating and thereby the productivity is increased; a solid oral formulation using the composition; and a method for producing the same.

Solution to Problem

In order to achieve the above-described objective, the present inventors conducted intensive investigations and found that when coating is performed using a PVA having a wider distribution of the degree of hydrolysis than other PVAs with the same degree of hydrolysis, stickiness tends to be less expressed during coating; that a film coating composition using a PVA which has a degree of hydrolysis of 85.0 to 89.0 mol % and which satisfies a specific requirement as an index of the distribution of the degree of hydrolysis is excellent in terms of productivity; and that the coating film of such a composition expresses excellent moistureproofing and gas barrier properties as is the case with the conventional PVAs. They have carried out further investigations and completed the present invention.

That is, the present invention relates to the following film coating compositions for solid oral formulations, etc.

[1] A film coating composition for a solid oral formulation, the composition containing a polyvinyl alcohol polymer having an average degree of hydrolysis of 85.0 to 89.0 mol % measured according to JIS K6726, the polyvinyl alcohol polymer satisfying the following requirement (A) or (B):

Requirement (A): the transparency of a liquid obtainable by adding 130.0 ml of 1-propanol to 100.0 g of a 5.0% by mass aqueous solution of the polyvinyl alcohol polymer followed by stirring is 50.0% or less at 20° C., or Requirement (B): a supernatant obtainable by adding 230.0 mL of 1-propanol to 100.0 g of a 5.0% by mass aqueous solution of the polyvinyl alcohol polymer followed by stirring and subsequent 24-hour standing at 20° C. has a concentration of 0.75% by mass or more.

[2] A film coating composition for a solid oral formulation, the composition containing a polyvinyl alcohol polymer having an average degree of hydrolysis of 85.0 to 89.0 mol % measured according to JIS K6726, the polyvinyl alcohol polymer satisfying the following requirements (A) and (B):

Requirement (A): the transparency of a liquid obtainable by adding 130.0 mL of 1-propanol to 100.0 g of a 5.0% by mass aqueous solution of the polyvinyl alcohol polymer followed by stirring is 50.0% or less at 20° C., and Requirement (B): a supernatant obtainable by adding 230.0 mL of 1-propanol to 100.0 g of a 5.0% by mass aqueous solution of the polyvinyl alcohol polymer followed by stirring and subsequent 24-hour standing at 20° C. has a concentration of 0.75% by mass or more.

[3] A film coating composition for a solid oral formulation, the composition containing a polyvinyl alcohol polymer having an average degree of hydrolysis of 85.0 to 89.0 mol % measured according to JIS K6726, the polyvinyl alcohol polymer satisfying the following requirement (C):

Requirement (C): when the polyvinyl alcohol polymer is subjected to liquid chromatography using a charged aerosol detector and a column, Acclaim™ 300 made by Thermo Scientific (Catalog number: 060266, Carbon load: 8%, Maximum pressure: 4500 psi, Particle diameter: 3 μm, Pore diameter: 300 Å, Stationary phase: C18, Surface area: 100 m$^2$/g, Length: 150 mm, Diameter: 4.6 mm, pH: 2.5 to 7.5, Material: Glass Lined Tubing) under the measurement conditions shown below and when a detected intensity after baseline correction at a retention time $T_i$ [min] is expressed as $P_i$ [pA], $T_n$ and $T_w$, which are represented by Formulae (1) and (2), respectively, using $T_i$ and $P_i$, satisfy Formula (3) provided that measurement data are obtained from 5.0 to 12.0 minutes of retention time with a data sampling period of 500 milliseconds.

Measurement Conditions:
  Concentration of aqueous solution of polyvinyl alcohol polymer: 0.1% by mass
  Volume of injected aqueous solution of polyvinyl alcohol polymer: 2 μL
  Column temperature: 50° C.
  Flow rate: 1.0 mL/min
  Eluent: Mixed solvent of water and methanol
  Gradient conditions of eluent: the mixing ratio of water and methanol in the eluent is changed at a constant rate from 95:5 to 15:85 during measurement time of 0 to 10 minutes, and is kept constant at 15:85 during measurement time of 10 to 15 minutes.

Formulae:

$$T_n = \Sigma(T_i \times P_i)/\Sigma(P_i) \quad \text{Formula (1)}$$

$$T_w = \Sigma(T_i^2 \times P_i)/\Sigma(T_i \times P_i) \quad \text{Formula (2)}$$

$$\{(T_w/T_n)-1\} \times 1000 > 20 \quad \text{Formula (3)}$$

[4] The film coating composition for a solid oral formulation according to any one of the above [1] to [3] characterized in that the polyvinyl alcohol polymer satisfies a requirement that a 4% by mass aqueous solution of the polyvinyl alcohol polymer has a viscosity of from 2.0 mPa·s to 10.0 mPa·s as measured according to JIS K6726.

[5] A solid oral formulation, which is a tablet containing a medicinal substance and being coated with the film coating composition according to any one of the above [1] to [4].

[6] A method for producing a solid oral formulation, the method comprising a step of applying or spraying an aqueous solution and/or a water-based solution containing the film coating composition according to any one of the above [1] to [4] onto a tablet containing a medicinal substance to coat the surface of the tablet with the film coating composition.

[7] The solid oral formulation according to the above [5], wherein the amount of the coating accounts for 1 to 10% by mass of the total mass of the tablet.

Advantageous Effects of Invention

According to the present invention, a film coating composition characterized in that the composition can be used for pharmaceutical formulations in Japan, the US, and Europe, that even when the composition is used for coating of tablets without any substance other than PVAs, the tablets do not tend to stick to each other and thereby the coating time can be shortened, and that the composition can form a coating film having an excellent moistureproofing property and a high water solubility; a solid oral formulation using the composition; and a method for producing the same are provided.

BRIEF DESCRIPTION OF DRAWING

FIG. 1 is a chart showing the detected intensities at retention times from 5.0 to 12.0 minutes measured by liquid chromatography of a PVA polymer having an average degree of hydrolysis of 88.2 mol % and a 4% by mass aqueous solution viscosity of 5.3 mPa·s.

DESCRIPTION OF EMBODIMENTS

Hereinafter, the present invention will be described in detail.

PVA Polymer

First, the PVA polymer used for the film coating composition for solid oral formulations will be described in detail.

The PVA polymer used in the present invention has an average degree of hydrolysis of 85.0 to 89.0 mol % and preferably has a wider distribution of the degree of hydrolysis than those of conventional PVA polymers.

The average degree of hydrolysis of the PVA polymer is measured according to the hydrolysis degree measuring method specified in JIS K6726.

In the present invention, two indices representing the distribution of the degree of hydrolysis may be used. The first index relates to a method comprising adding a certain amount of 1-propanol to an aqueous solution containing a PVA polymer completely dissolved therein, followed by mixing. The distribution of the degree of hydrolysis can be known from the amount of PVA components that precipitate and the amount of PVA components that do not precipitate and can be specified by the transparency and the concentration of the resulting aqueous solution. Regarding this index used in the present invention, a PVA polymer that satisfies either one or both of the following requirements (A) and (B) is preferably used. Hereinafter, the meanings of these requirements will be described.

"Requirement (A): the transparency of a liquid obtainable by adding 130.0 mL of 1-propanol to 100.0 g of a 5.0% by mass aqueous solution of the polyvinyl alcohol polymer followed by stirring is 50.0% or less at 20° C."

Preferably, the stirring is performed uniformly.

The method for the stirring is not particularly limited, and for example, preferred is stirring at 500 rpm using a stirrer.

The drip rate of 1-propanol is not particularly limited, and is preferably 10 mL/min, for example.

The above "transparency of the liquid at 20° C." means the transparency of the liquid after left stand at 20° C. for a predetermined time (for example, 30 minutes or longer, about 30 minutes to 1 hour) until air bubbles have escaped from the liquid and become visually unnoticeable.

The transparency is preferably 30.0% or less, and more preferably 20.0% or less.

Here, the measurement of the transparency is performed using a spectrophotometer specified in JIS K0115, by a method in which the transmittance at 430 nm is determined using a quartz or glass absorption cell having an optical path length of 20 mm and water as the control.

The meaning of the transparency determined here is as follows. Since a highly hydrolyzed PVA component is hardly dissolved in 1-propanol, adding a certain amount of 1-propanol to an aqueous solution of a PVA polymer results in precipitation of the highly hydrolyzed PVA component, which causes turbidity. That is, a transparency of 50.0% or less under the above conditions means a high content of such a highly hydrolyzed component, i.e. a wide distribution at the higher hydrolysis degree side.

"Requirement (B): a supernatant obtainable by adding 230.0 mL of 1-propanol to 100.0 g of a 5.0% by mass aqueous solution of the polyvinyl alcohol polymer followed by stirring and subsequent 24-hour standing at 20° C. has a concentration of 0.75% by mass or more."

Preferably, the stirring is performed uniformly.

The method for the stirring is not particularly limited, and for example, preferred is stirring at 500 rpm using a stirrer.

The drip rate of 1-propanol is not particularly limited, and is preferably 10 mL/min, for example.

The concentration of the supernatant is preferably 0.75% by mass or more, and more preferably 0.80% by mass or more.

The supernatant can be obtained by collecting 30 to 60% by mass of the total amount of a liquid layer obtained by adding 23.0 mL of 1-propanol to 100.0 g of a 5.0% by mass aqueous solution of the polyvinyl alcohol polymer followed by stirring and subsequent 24-hour standing at 20° C.

The concentration of the supernatant can be measured, for example, by the following method. Using a dropper, about 80 g of the supernatant is carefully collected not to include any precipitating components, placed in a petri dish, and then dried at 60° C. for 5 hours and at 105° C. for 24 hours. The concentration of concern is calculated based on the difference between the weights before and after the drying.

The meaning of the supernatant concentration determined here is as follows. Since a PVA component with a low degree of hydrolysis is hardly precipitated by 1-propanol added thereto, even when a certain amount of 1-propanol is added to an aqueous solution of a PVA polymer containing such a PVA component, the PVA component with a low degree of hydrolysis remains dissolved in the solution. Therefore, the supernatant concentration of 0.75% by mass or more means a wide distribution at the lower hydrolysis degree side.

The PVA polymer used for the film coating composition of the present invention usually has an average degree of hydrolysis within the range of 85.0 to 89.0 mol %, and satisfies the requirement (A), i.e., has a wipe distribution at the higher hydrolysis degree side or satisfies the requirement (B), i.e., has a wide distribution at the lower hydrolysis degree side. Preferably, the PVA polymer satisfies both the requirement (A) and the requirement (B), i.e., has a wide distribution at both the higher hydrolysis degree side and the lower hydrolysis degree side.

The PVA polymer used for the film coating composition of the present invention satisfies the requirement (A) and/or the requirement (B), and therefore has a wide distribution of the degree of hydrolysis.

A PVA polymer of which the transparency measured under the conditions of the requirement (A) is 50.0% or less is preferable because in a coating test using such a PVA polymer, tablets do not tend to stick to each other, coating defects can be prevented, and coating time can be shortened.

Also, a PVA polymer of which the supernatant concentration measured under the conditions of the requirement (B) is 0.75% by mass or more is preferable because in a coating test using such a PVA polymer, tablets do not tend to stick to each other, coating defects can be prevented, and coating time can be shortened.

The second index representing the distribution of the degree of hydrolysis used in the present invention relates to a method comprising subjecting a PVA polymer to liquid chromatography using a charged aerosol detector, in which method the distribution is shown by the relation between the retention time and the detected intensity. Regarding this index used in the present invention, a PVA polymer that satisfies the following requirement (C) is preferably used. Hereinafter, the meaning of the requirement will be described.

"Requirement (C): when the polyvinyl alcohol polymer is subjected to liquid chromatography using a charged aerosol detector and a column, Acclaim™ 300 made by Thermo Scientific (Catalog number: 060266, Carbon load: 8%, Maximum pressure: 4500 psi, Particle diameter: 3 μm, Pore diameter: 300 Å, Stationary phase: C18, Surface area: 100 m$^2$/g, Length: 150 mm, Diameter: 4.6 mm, pH: 2.5 to 7.5, Material: Glass Lined Tubing) under the measurement conditions shown below and when a detected intensity after baseline correction at a retention time $T_i$ [min] is expressed as $P_i$ [pA], $T_n$ and $T_w$, which are represented by Formulae (1) and (2), respectively, using $T_i$ and $P_i$, satisfy Formula (3) provided that measurement data are obtained from 5.0 to 12.0 minutes of retention time with a data sampling period of 500 milliseconds.

Measurement Conditions:
  Concentration of aqueous solution of polyvinyl alcohol polymer: 0.1% by mass
  Volume of injected aqueous solution of polyvinyl alcohol polymer: 2 μL
  Column temperature: 50° C.
  Flow rate: 1.0 mL/min
  Eluent: Mixed solvent of water and methanol Gradient conditions of eluent: the mixing ratio of water and methanol in the eluent is changed at a constant rate from 95:5 to 15:85 during measurement time of 0 to 10 minutes, and is kept constant at 15:85 during measurement time of 10 to 15 minutes.

Formulae:

$$T_n = \Sigma(T_i \times P_i)/\Sigma(P_i) \quad \text{Formula (1)}$$

$$T_w = \Sigma(T_i^2 \times P_i)/\Sigma(T_i \times P_i) \quad \text{Formula (2)}$$

$$\{(T_w/T_n)-1\} \times 1000 > 20 \quad \text{Formula (3)}"$$

In the above requirement, the charged aerosol detector to be used and the liquid chromatography are not particularly limited, and for example, as the charged aerosol detector, CORONA VEO made by Thermo Scientific can be used. Also, for the liquid chromatography, ULTIMATE 3000 made by Thermo Scientific can be used.

When a PVA polymer is subjected to the measurement by liquid chromatography using a charged aerosol detector, a PVA-containing sample solution is eluted from the column and introduced into the charged aerosol detector, the PVA sample solution is subjected to spraying and drying to form microparticles, and the PVA microparticles are charged with $N^+$ ions and measured for detection.

In the present invention, the column used for the liquid chromatography is usually a reverse phase ODS column filled with porous silica spheres surface-modified with chemically bonded octadecylsilyl groups as the stationary phase, namely, Acclaim™ 300 made by Thermo Scientific (Catalog number: 060266, Carbon load: 8%, Maximum pressure: 4500 psi, Particle diameter: 3 µm, Pore diameter: 300 Å, Stationary phase: C18, Surface area: 100 m²/g, Length: 150 mm, Diameter: 4.6 mm, pH: 2.5 to 7.5, Material: Glass Lined Tubing).

The PVA polymer as a test sample is dissolved in purified water, and is measured in the form of an aqueous solution. The concentration of the PVA polymer aqueous solution is usually 0.1% by mass.

Under usual measurement conditions, the flow rate is 1 mL/min, the column temperature is 50° C., and the amount of injected PVA polymer aqueous solution is 2 µL.

As the eluent, a mixed solvent of water and methanol is usually used.

Usually, gradient elution is carried out for the measurement.

The gradient condition changed over measurement time is usually as follows. At measurement time 0 minutes, the mixing ratio of water and methanol in the eluent is 95:0. From 0 to 10 minutes, the ratio is changed at a certain rate (for example, water is reduced by 8% per minute and methanol is increased by 8% per minute) so that the ratio becomes 15:85 at 10 minutes. Then, from 10 to 15 minutes, the ratio of water and methanol in the eluent is kept constant at 15:85.

In the time period in which water accounts for a high percentage of the eluent, components having high degrees of hydrolysis in the PVA polymer are eluted, and as the percentage of methanol in the eluent increases, components having low degrees of hydrolysis in the PVA polymer start to be gradually eluted.

If any dead space exists in the column, the 0 to 10 minutes gradient may be insufficient for accurate measurement. To eliminate such inaccuracy, usually, the eluent is passed for additional 5 minutes under the conditions described above.

After 15 minutes, to flush out components having low degrees of hydrolysis and remaining in the column, an eluent in which the ratio of water and methanol is 5:95 is preferably passed for 5 minutes. In the cases where another measurement of a PVA polymer is subsequently carried out, the column is preferably regenerated to the initial equilibrium state by passing an eluent of water and methanol at a constant ratio of 95:5 for about 7 to 10 minutes.

By measuring a sample of the PVA polymer under the above conditions, a chart showing the correlation between the retention time and the detected intensity can be obtained. After baseline correction, i.e., by deducting so-called baseline peaks obtained in a measurement without injecting any sample solution under the above measurement conditions, a chart showing the detected intensity at each retention time is obtained.

FIG. 1 shows a chart showing the detected intensities at retention times from 5.0 to 12.0 minutes of a PVA (JP-05 made by Japan VAM & POVAL) having an average degree of hydrolysis of 88.2 mol % as measured according to JIS K6726 and a 4% by mass aqueous solution viscosity of 5.3 mPa·s as measured according to JIS K6726.

In the present invention, it is preferred that the data sampling period, which is the frequency at which a data processor receives signals from the detector, is 500 milliseconds, i.e., the data processor receives one signal intensity for every 0.5 second, and more preferred is that the data sampling period is less than 2 sec. By plotting the data, a chart as shown in FIG. 1 is obtained.

Under the liquid chromatography conditions, in the early period of the measurement, when water accounts for a high percentage of the eluent, components having high degrees of hydrolysis in the sample PVA polymer are eluted. Then, as the percentage of methanol in the eluent increases, partially hydrolyzed components are eluted. In a chart of ion intensity detected by a Corona detector at each retention time, a PVA polymer having a narrow distribution of the degree of hydrolysis shows a sharp peak of which the peak top appears near 9.5 minutes of the retention time. When a PVA polymer having the same degree of hydrolysis but having a wider distribution of the degree of hydrolysis is measured, a wider peak having its peak top at the same retention time is obtained.

Provided that the detected intensity at each retention time $T_i$ [min] is expressed as $P_i$ [pA], $T_n$ and $T_w$ can be represented as shown in Formulae (1) and (2) for all the collected data of detected intensities at retention times. As used herein, $T_n$ and $T_w$ correspond to the number average molecular weight $M_n$ and the weight average molecular weight $M_w$ in the molecular weight distribution measurement using gel permeation chromatography (hereinafter abbreviated as GPC), respectively.

Using these $T_n$ and $T_w$, i.e., using $T_w/T_n$ corresponding to so-called polydispersity $M_w/M_n$ in molecular weight distribution measurement, the distribution of the degree of hydrolysis can be specified as in Formula (3).

The value of $\{(T_w/T_n)-1\} \times 1000$ of Formula (3) is usually greater than 20, preferably greater than 25 (for example, 25 to 90), and more preferably greater than 30 (for example, 30 to 85).

That is, a greater value represented by $\{(T_w/T_n)-1\} \times 1000$ means a wider distribution of the degree of hydrolysis of the PVA polymer, and when coating is performed using a PVA polymer of which this value is greater than 20, tablets do not tend to stick to each other, therefore the spraying speed in the coating can be increased, and thus the coating time can be shortened.

In contrast, a PVA polymer of which the value of $\{(T_w/T_n)-1\} \times 1000$ is 20 or less has a narrow distribution of the degree of hydrolysis, and when coating test is performed using such a PVA polymer, tablets tend to stick to each other, coating defects may occur, and the coating time may be prolonged.

The PVA polymer used in the present invention satisfies at least one, preferably two, more preferably three of the above requirements (A) to (C).

Heretofore, quantitative measurement of the distribution of the degree of hydrolysis has been difficult, but in the present invention, the method described in the requirement (A), (B), or (C) was found to enable successful measurement of the distribution of the degree of hydrolysis.

The method for producing the PVA polymer used in the present invention may be a known method in which, for example, a polymer comprising vinyl ester monomers is saponified, and examples of the vinyl ester monomers include vinyl acetate.

The method for polymerization of vinyl acetate is not particularly limited, and examples thereof include publicly known methods, such as bulk polymerization, solution polymerization, suspension polymerization, emulsion polymerization, etc. Industrially preferred is solution polymerization using methanol as the solvent. For the solution polymerization, publicly known initiators, such as peroxide initiators and azo initiators, can be used, and by changing the blending ratio of vinyl acetate and methanol, and by changing the polymerization yield, the degree of polymerization of resulting polyvinyl acetate can be adjusted. Commercially available polyvinyl acetate resin can also be used as a raw material for obtaining the PVA polymer of the present invention.

As the saponification method of the obtained polyvinyl acetate, the conventionally known saponification methods using an alkali catalyst or an acid catalyst may be used. Among them, industrially preferred is the method in which an alkali, such as sodium hydroxide, is added to a solution of polyvinyl acetate in methanol or to a solution of polyvinyl acetate in a mixture of methanol, water, and methyl acetate with stirring for alcoholysis of the acetyl groups of the polyvinyl acetate.

Then, after the resulting block-like, gel-like, or granular substance is pulverized and the added alkali is neutralized as needed, the solid matter is separated from the liquid and dried to give a PVA polymer.

The PVA polymer used in the present invention can be produced by saponification performed in a less uniform system than usual. Specific examples of such a method include a method in which saponification is performed using a methanol solution of polyvinyl acetate at a higher concentration (for example, 55% by mass or higher), a method in which saponification is performed with mixing at a lower stirring speed (for example, 20 rpm or lower) after alkali addition, a method in which saponification is performed with mixing for a shorter stirring time after alkali addition, a method in which saponification is performed in a shorter time by using an increased amount of alkali, and a method in which saponification is performed in a saponification system provided with temperature gradient or temperature distribution achieved by, for example, adjusting the temperatures of the methanol solution of polyvinyl acetate and of the alkali to be added.

In addition, other methods including a method in which saponification is performed by adding a solvent having an influence on the saponification reaction rate, such as water, methyl acetate, or the like in a non-uniform manner may be employed. By such operations, the degree of hydrolysis of the obtained PVA polymer tends to be non-uniform, and as a result, a PVA polymer having the same average degree of hydrolysis as conventional PVA polymers but having a wider distribution of the degree of hydrolysis than those of conventional PVA polymers can be produced.

In addition to the above methods, a PVA in which two or more kinds of PVA powders having different degrees of hydrolysis from each other are blended so as to achieve a desired weighted average degree of hydrolysis can be used as an embodiment of the PVA polymer of the present invention.

In this case, the PVA polymer can be obtained by, for example, mixing two kinds of PVAs, PVA (a) and PVA (b).

The average degree of hydrolysis or PVA (a) measured according to the testing method specified in JIS K6726 is, for example, 85 mol % or higher (for example, 85 to 99 mol %), preferably 88 mol % or higher (for example, 88 to 99 mol %), more preferably 90 mol % or higher (for example, 90 to 99 mol %), and still more preferably 92 mol % or higher (for example, 92 to 99 mol %).

The average degree of hydrolysis of PVA (b) is, for example, 99 mol % or lower (for example, 60 to 99 mol %), preferably 95 mol % or lower (for example, 60 to 95 mol %), more preferably 90 mol % or lower (for example, 65 to 90 mol %), and still more preferably 88 mol % or lower (for example, 65 to 88 mol %).

The mixing ratio of PVA (a) and PVA (b) is, for example, 5:95 to 95:5, preferably 10:90 to 90:10, more preferably 15:85 to 85:15, and still more preferably 20:80 to 80:20 on the mass basis.

Also, the weighted average degree of hydrolysis of the PVA polymer obtained by mixing PVA (a) and PVA (b) (i.e., weighted average degree of hydrolysis $C=(A \times A'+B \times B')/100$ provided that the degree of hydrolysis of PVA (a) is A mol %, the degree of hydrolysis of PVA (b) is B mol %, and the mixing ratio of PVA (a) and PVA (b) is A':B') is, for example, 83 to 89 mol %, preferably 85 to 89 mol %, and more preferably 86 to 89 mol %.

Since the PVA polymer used in the present invention is mainly used for film coating compositions for pharmaceutical solid oral formulations, the degree of hydrolysis is required to be within the standards of degree of hydrolysis of PVA specified in the three official specifications, namely, Japanese Pharmaceutical Excipients, the US Pharmacopeia, and the European Pharmacopoeia, and also, quick dissolution in the living body must be achieved. Therefore, the degree of hydrolysis should be 85.0 to 89.0 mol %. A PVA polymer of which the degree of hydrolysis is less than 85.0 mol % cannot be used as a material for pharmaceutical formulations to be on the global market. Also, such a PVA polymer having a high percentage of hydrophobic groups is less hydrophilic and tends to precipitate at a high temperature when an aqueous solution is prepared, resulting in difficult handling. Also, a PVA polymer of which the degree of hydrolysis is more than 89.0 mol % also cannot be used as a material for pharmaceutical formulations to be on the global market. Such a PVA polymer having an increased amount of hydroxyl groups, i.e., having increased crystallinity, is less soluble in water and tends to have a lower dissolution rate when used for film coating of a pharmaceutical solid oral formulation.

The degree of polymerization of the PVA polymer used in the present invention is not particularly limited, but the 4% by mass aqueous solution viscosity (measured according to JIS K6726) is preferably 2.0 to 10.0 mPa·s, more preferably 3.0 to 7.0 mPa·s.

A PVA polymer of which the 4% by mass aqueous solution viscosity is 2.0 mPa·s or higher is preferable because the film formed on the tablet surface after coating will have a high strength. A PVA polymer of which the 4% by mass aqueous solution viscosity is 10.0 mPa·s or less is preferable because the spraying speed in the coating can be increased due to the low viscosity, resulting in improved productivity.

To the coating composition of the present invention, additives may be added as needed, and examples thereof include, a medicinal substance usually used for pharmaceutical formulations; plasticizers, such as glycerol, polyethylene glycol, propylene glycol, and triethyl citrate; inorganic compounds, such as titanium oxide, talc, and colloidal silica; lubricants, such as magnesium stearate, calcium stearate, and stearic acid; polymers, such as hydroxypropylmethylcellulose and hydroxypropylcellulose; a surfactant; a colorant; a pigment; a sweetener; a coating agent; a defoaming agent; a pH adjuster; etc. The additives may be used alone or as a combination of two or more thereof. When the additives are added, the amount thereof is preferably 100 parts by mass or less, more preferably 50 parts by mass or less, and still more preferably 10 parts by mass or less, relative to 100 parts by mass of the PVA polymer.

Solid Oral Formulation

The solid oral formulation of the present invention comprises at least a tablet containing a medicinal substance and the film coating composition of the present invention coating the tablet.

The medicinal substance is not particularly limited as long as the substance can be orally administered.

Various additives conventionally used in the field may be blended into the tablet containing a medicinal substance, and examples of the additives include an excipient, a binder, a disintegrant, a lubricant, a dispersant, a solubilizing agent for a pharmaceutical compound, etc. Examples of the excipient include sugars, such as sucrose, lactose, mannitol, and glucose, starch, crystalline cellulose, calcium phosphate, and calcium sulfate. Examples of the binder include polyvinyl alcohol, polyacrylic acid, polymethacrylic acid, polyvinyl pyrrolidone, glucose, sucrose, lactose, maltose, dextrin, sorbitol, mannitol, hydroxyethylcellulose, hydroxypropylmethylcellulose, hydroxypropylcellulose, macrogols, gum arabic, gelatin, agar, and starch. Examples of the disintegrant include low substituted hydroxypropylcellulose, carmellose or a salt thereof, croscarmellose sodium, sodium carboxymethyl starch, cross-linked polyvinyl pyrrolidone, crystalline cellulose, and crystalline cellulose carmellose sodium. Examples of the lubricant and the dispersant include talc, magnesium stearate, calcium stearate, colloidal silica, stearic acid, waxes, hardened oils, polyethylene glycol, and sodium benzoate. Examples of the solubilizing agent for a pharmaceutical compound include organic acids, such as fumaric acid, succinic acid, malic acid, and adipic acid, etc. The additives may be used alone or as a combination of two or more thereof. The amounts of these additives can be suitably determined depending on the type of the medicinal substance etc.

The solid oral formulation of the present invention can be prepared by coating a tablet containing a medicinal substance with the film coating composition of the present invention.

Next, the method for producing the solid oral formulation of the present invention will be described.

The method for coating a tablet with the film coating composition of the present invention is not particularly limited, and conventionally known coating means can be used. Spray coating is generally performed, for which a pan coater, a drum coater, or the like can be used, and also air spray, airless spray, or the like can be used as an accompanying spray device.

The method for coating a tablet with the film coating composition of the present invention include the following method. For example, a solution is prepared by dissolving or dispersing the film coating composition of the present invention, to which one or more additives are added as needed, in water, an organic solvent such as ethanol, or a mixture thereof, and using the above-mentioned coater, the solution is applied or sprayed onto the surface of a tablet containing a medicinal substance, and is dried at the same time to coat the tablet.

The amount of the film coating composition applied to the tablet surface depends on the type, the shape, the size, and the surface condition of the solid formulation, and also on the properties of the medicinal substance and the additive(s) contained in the solid formulation, but is preferably 1 to 10% by mass, more preferably 1 to 7% by mass, and particularly preferably 2 to 6% by mass, relative to the total amount of the tablet. When the coating amount is too little, the tablet cannot be completely coated, and sufficient moistureproofing effect, oxygen barrier property, and odor masking effect cannot be obtained. On the other hand, when the coating amount is too much, the problem is that longer time is required for the coating.

The solid oral formulation of the present invention may be a multilayered film coated solid oral formulation, the film comprising different components and being formed by, for example, providing an undercoat formed of a composition comprising various polymers that are usually used for coating of pharmaceutical formulations, such as hydroxypropylmethylcellulose, under the film layer formed of the film coating composition of the present invention, or by providing an overcoat formed of a composition comprising various polymers that are usually used for coating of pharmaceutical formulations on the film layer formed of the film coating composition of the present invention.

EXAMPLES

Hereinafter, the present invention will be described in more detail by reference to Examples, but the present invention is not limited thereto.

In the following Examples and Comparative Examples, "%" and "part" are on the mass basis unless otherwise stated.

Liquid Chromatography Measurement Conditions
  Detector: Charged aerosol detector
  Column: Acclaim™ 300 made by Thermo Scientific (Catalog number: 060266, Carbon load: 8%, Maximum pressure: 4500 psi, Particle diameter: 3 μm, Pore diameter: 300 Å, Stationary phase: C18, Surface area: 100 m$^2$/g, Length: 150 mm, Diameter: 4.6 mm, pH: 2.5 to 7.5, Material: Glass Lined Tubing)
  Concentration of aqueous solution of PVA polymer: 0.1% by mass
  Volume of injected aqueous solution of PVA polymer: 2 μL
  Column temperature: 50° C.
  Flow rate: 1.0 mL/min
  Eluent: Mixed solvent of water and methanol
  Gradient conditions of eluent: the mixing ratio of water and methanol in the eluent is changed at a constant rate from 95:5 to 15:85 (water is reduced by 8% per minute and metnanol is increased by 8% per minute) during measurement time of 0 to 10 minutes, and is kept constant at 15:85 during measurement time of 10 to 15 minutes.

When the PVA polymer is measured under the above conditions and when a detected intensity after baseline correction at a retention time $T_i$ [min] is expressed as $P_i$ [pA], $T_n$ and $T_w$, which are represented by Formulae (1) and (2), respectively, using $T_i$ and $P_i$, satisfy Formula (3) provided that measurement data are obtained from 5.0 to 12.0 minutes of retention time with a data sampling period of 500 milliseconds.

Formulae:

$$T_n = \Sigma(T_i \times P_i)/\Sigma(P_i) \qquad \text{Formula (1)}$$

$$T_w = \Sigma(T_i^2 \times P_i)/\Sigma(T_i \times P_i) \qquad \text{Formula (2)}$$

$$\{(T_w/T_n)-1\} \times 1000 > 20 \qquad \text{Formula (3)}$$

Method for Synthesis of PVA Polymer

Comparative Synthesis Example 1

A commercially available polyvinyl acetate resin (JMR-30LL made by Japan VAM & POVAL, polymerization degree: 590) was vacuum dried at 100° C. for removal of moisture, and then dissolved in methanol to give a 46% by mass methanol solution of polyvinyl acetate. To 500 parts by mass of this solution warmed to 40° C., 16 parts by mass of a 3% by mass methanol solution of sodium hydroxide adjusted to 35° C. was added. The mixture was stirred using a propeller-type mixing blade at 300 rpm for 1 minute and then left stand at 40° C. for 40 minutes for saponification. The obtained gel-like material was pulverized, was immersed in a mixed solvent of 570 parts by mass of methanol, 230 parts by mass of methyl acetate, and 17 parts by mass of water, and was stirred at a slow speed at 40° C. for additional 1 hour for saponification. The reaction mixture was neutralized with 1% by mass aqueous solution of acetic acid so that the pH became 8 to 9. The solid matter was separated from the liquid, and dried at 60° C. for 8 hours to give a PVA polymer.

The PVA polymer had an average degree of hydrolysis of 88.3 mol % and a 4% by mass aqueous solution viscosity of 5.3 mPa·s, each of which was measured by the method specified in JIS K6726. The transparency of a liquid obtained by adding 130 mL of 1-propanol to 100 g of a 5.0% by mass aqueous solution of the PVA polymer followed by uniform stirring was 99.4% at 20° C., and the supernatant obtained by adding 230 mL of 1-propanol to 100 g of a 5.0% by mass aqueous solution of the PVA polymer followed by uniform stirring and subsequent 24-hour standing at 20° C. has a concentration of 0.62% by mass. Further, the PVA polymer was subjected to LC-CAD under the above measurement conditions, and the obtained value of Formula (3): $\{(T_w/T_n)-1\} \times 1000$ was 12. The average degree of hydrolysis, the 4% by mass aqueous solution viscosity, the transparency and the supernatant concentration after the addition of 1-propanol, and the value of Formula (3) based on LC-CAD measurement regarding Comparative Synthesis Example 1 are shown in Table 1.

Synthesis Example 1

A PVA polymer was obtained in the same manner as in Comparative Synthesis Example 1 except that the stirring after the addition of the sodium hydroxide solution to the methanol solution of polyvinyl acetate was performed at 60 rpm for 30 seconds for achieving less uniform mixing than in usual conditions.

The PVA polymer had an average degree of hydrolysis of 88.2 mol % and a 4% by mass aqueous solution viscosity of 5.2 mPa·s, each or which was measured by the method specified in JIS K6726. The transparency of a liquid obtained by adding 130 mL of 1-propanol to 100 g of a 5.0% by mass aqueous solution of the PVA polymer followed by uniform stirring was 18.5% at 20° C., and the supernatant obtained by adding 230 mL of 1-propanol to 100 g of a 5.0% by mass aqueous solution of the PVA polymer followed by uniform stirring and subsequent 24-hour standing at 20° C. has a concentration of 0.83% by mass. Further, the PVA polymer was subjected to LC-CAD under the above measurement conditions, and the obtained value of Formula (3): $\{(T_w/T_n)-1\} \times 1000$ was 43. The average degree of hydrolysis, the 4% by mass aqueous solution viscosity, the transparency and the supernatant concentration after the addition of 1-propanol, and the value of Formula (3) based on LC-CAD measurement regarding Synthesis Example 1 are shown in Table 1.

Synthesis Example 2

A PVA polymer was obtained in the same manner as in Comparative Synthesis Example 1 except that the stirring after the addition of the sodium hydroxide solution to the methanol solution of polyvinyl acetate was performed at 20 rpm for 60 seconds for achieving less uniform mixing than in usual conditions.

The average degree of hydrolysis, the 4% by mass aqueous solution viscosity, the transparency and the supernatant concentration after the addition of 1-propanol, and the value of Formula (3) based on LC-CAD measurement regarding Synthesis Example 2 are shown in Table 1.

Synthesis Example 3

A PVA polymer was obtained in the same manner as in Comparative Synthesis Example 1 except that, in the saponification, the concentration of the methanol solution of polyvinyl acetate was 55% by mass and the amount of the sodium hydroxide solution added to 500 parts by mass of this polyvinyl acetate solution was 23 parts by mass. The average degree of hydrolysis, the 4% by mass aqueous solution viscosity, the transparency and the supernatant concentration after the addition of 1-propanol, and the value of Formula (3) based on LC-CAD measurement regarding Synthesis Example 3 are shown in Table 1.

Synthesis Example 4

A PVA polymer was obtained in the same manner as in Comparative Synthesis Example 1 except that, in the saponification, a band heater was attached to the upper half of the container of the mixed solution of the methanol solution of polyvinyl acetate and sodium hydroxide and heated to 50° C. to provide temperature gradient so that the upper half was at 50° C. and the lower half was at room temperature (25° C.) and that the mixture was left stand for 50 minutes. The average degree of hydrolysis, the 4% by mass aqueous solution viscosity, the transparency and the supernatant concentration after the addition of 1-propanol, and the value of Formula (3) based on LC-CAD measurement regarding Synthesis Example 4 are shown in Table 1.

Synthesis Example 5

A PVA polymer was obtained in the same manner as in Comparative Synthesis Example 1 except the following. The 500 parts by mass of the 46% by mass methanol solution of polyvinyl acetate was divided into two (250 parts by mass each), placed in different containers, and warmed to 40° C. The 3% by mass methanol solution of sodium hydroxide adjusted to 35° C. was added, in an amount of 10 parts by mass to one container and in an amount of 6 parts by mass to the other container. Both were simultaneously stirred at 300 rpm for 1 minute and then left stand at 40° C. for 40 minutes to allow saponification to proceed separately. The obtained gel-like matters were combined and pulverized together. The average degree of hydrolysis, the 4% by mass aqueous solution viscosity, the transparency and the supernatant concentration after the addition of 1-propanol, and the value of Formula (3) based on LC-CAD measurement regarding Synthesis Example 5 are shown in Table 1.

Synthesis Example 6

A commercially available PVA resin (JL-05E made by Japan VAM & POVAL, degree of hydrolysis: 80.2 mol %, 4% by mass aqueous solution viscosity: 5.1 mPa·s) in an amount of 40 parts by mass and another commercially available PVA resin (JT-05 made by Japan VAM & POVAL, degree of hydrolysis: 94.0 mol %, 4% by mass aqueous solution viscosity: 5.6 mPa·s) in an amount of 60 parts by mass were placed in a polyethylene bag, and the bag was shaken about 100 times to uniformly mix the PVA powders to give a PVA polymer having a wide distribution of the degree of hydrolysis. The average degree of hydrolysis, the 4% by mass aqueous solution viscosity, the transparency and the supernatant concentration after the addition of 1-propanol, and the value of Formula (3) based on LC-CAD measurement regarding Synthesis Example 6 are shown in Table 1.

Synthesis Example 7

A commercially available PVA resin (JP-05 made by Japan VAM & POVAL, degree of hydrolysis: 87.5 mol %, 4% by mass aqueous solution viscosity: 5.3 mPa·s) in an amount of 90 parts by mass and another commercially available PVA resin (JT-05 made by Japan VAM & POVAL, degree of hydrolysis: 94.0 mol %, 4% by mass aqueous solution viscosity: 5.6 mPa·s) in an amount of 10 parts by mass were placed in a polyethylene bag, and the bag was shaken about 100 times to uniformly mix the PVA powders to give a PVA polymer having a wide distribution of the degree of hydrolysis. The average degree of hydrolysis, the 4% by mass aqueous solution viscosity, the transparency and the supernatant concentration after the addition of 1-propanol, and the value of Formula (3) based on LC-CAD measurement regarding Synthesis Example 7 are shown in Table 1.

Synthesis Example 8

A commercially available PVA resin (JL-05E made by Japan VAM & POVAL, degree of hydrolysis: 80.2 mol %, 4% by mass aqueous solution viscosity: 5.1 mPa·s) in an amount of 8 parts by mass and another commercially available PVA resin (JP-05 made by Japan VAM & POVAL, degree of hydrolysis: 88.8 mol %, 4% by mass aqueous solution viscosity: 5.3 mPa·s) in an amount of 92 parts by mass were placed in a polyethylene bag, and the bag was shaken about 100 times to uniformly mix the PVA powders to give a PVA polymer having a wide distribution of the degree of hydrolysis. The average degree of hydrolysis, the 4% by mass aqueous solution viscosity, the transparency and the supernatant concentration after the addition of 1-propanol, and the value of Formula (3) based on LC-CAD measurement regarding Synthesis Example 8 are shown in Table 1.

Coating Conditions
  Device: HICOATER (HC-FZ-Labo made by Freund Corp.)
  Amount of charged tablets: 1000 g
  Supply air temperature: 70 to 80° C.
  Exhaust air temperature: 44 to 52° C.
  Supply air flow rate: 0.6 m³/min
  Number of spray guns: 1
  Spray gun air flow (atomized air): 30 L/min
  Spray gun air flow (pattern air): 9 L/min
  Spraying speed: adjusted by discharge rate of tubing pump
  Pan rotation speed: 18 rpm Evaluation of Coating Time In a coating test, the spraying speed at which the coating solution was applied by spraying was initially set at 3.0 g/min, and the speed was gradually increased until sticking between tablets or sticking between tablets and the pan occurred. Then, the spraying speed was lowered to the extent that neither sticking between tablets nor sticking between tablets and the pan was observed. After confirming the absence of sticking during 10-minute spraying at the same speed, the speed was determined so be the maximum spraying speed. In the cases where sticking between tablets or sticking between tablets and the pan occurred at the initial spraying speed of 3.0 g/min, the spraying speed was gradually lowered. After confirming the absence of sticking during 10-minute, spraying at the same speed, the speed was determined to be the maximum spraying speed. In either case, from the maximum spraying speed, the shortest coating time to provide tablets with 3% by mass coating on the solid basis was calculated.

Evaluation of Water Vapor Transmission Rate

A solution or dispersion of the coating composition having a concentration of 12% by mass on the solid basis was cast on a PET sheet and then dried in a constant temperature and humidity chamber at 25° C. and 65% RH to give a film having a thickness of 100 μm. The water vapor transmission rate at 25° C. and 65% RH of the obtained film was measured using a water vapor permeation analyzer L80-5000 (made by Systech Instruments) by a method according to JIS K7129.

Example 1

To 220 parts by mass of purified water, 30 parts by mass of the PVA polymer of Synthesis Example 1 was added, and stirred for 1 hour while warmed to 80° C. to prepare a coating solution (PVA polymer concentration: 12% by mass). Using this coating solution, a test of coating on uncoated tablets mainly made of lactose and cornstarch was performed to evaluate the maximum spraying speed, the shortest coating time, and the water vapor transmission rate of the coating composition.

The maximum spraying speed of the film coating solution of the PVA polymer of Synthesis Example 1 was 4.85 g/min, and the coating time for 3% by mass coating was 52 minutes. The water vapor transmission rate was 32 g/m²·day. The results are shown in Table 2.

Examples 2 to 8

The coating test was performed in the same manner as in Example 1 except that one of the PVA polymers of Synthesis Examples 2 to 8 was used instead of the PVA polymer of Synthesis Example 1 to evaluate the maximum spraying speed, the shortest coating time, and the water vapor transmission rate. The results are shown in Table 2.

Comparative Example 1

The coating test was performed in the same manner as in Example 1 except that the PVA polymer of Comparative Synthesis Example 1 was used instead of the PVA polymer of Synthesis Example 1 to evaluate the maximum spraying speed, the shortest coating time, and the water vapor transmission rate. The results are shown in Table 2.

Comparative Example 2

The coating test was performed in the same manner as in Example 1 except that a commercially available partially hydrolyzed PVA polymer (JP-05 made by Japan VAM & POVAL, degree of hydrolysis: 88.2 mol %, 4% by mass aqueous solution viscosity: 5.3 mPa·s) was used instead of the PVA polymer of Synthesis Example 1 to evaluate the maximum spraying speed, the shortest coating time, and the water vapor transmission rate. The results are shown in Table 2. The transparency and the supernatant concentration after the addition of 1-propanol, and the value of Formula (3) based on LC-CAD measurement regarding the coating solution of JP-05 used are shown in Table 1.

Comparative Example 3

A commercially available partially hydrolyzed PVA polymer (JP-05 made by Japan VAM & POVAL, degree of hydrolysis: 88.2 mol %, 4% by mass aqueous solution viscosity: 5.3 mPa·s) in an amount of 24 parts by mass and PEG6000 (made by Wako Pure Chemical Industries, average molecular weight: 5400 to 6600) in an amount of 6 parts by mass were placed in a polyethylene bag, and the bag was shaken more than 100 times to give a uniform film coating composition. This film coating composition was added to 220 parts by mass of purified water, stirred for 1 hour while warmed to 80° C., and then cooled for 30 minutes to prepare a coating solution (PVA:PEG6000=8:2, aqueous solution concentration: 12% by mass). The coating test was performed in the same manner as in Example 1 except that this coating solution was used to evaluate the maximum spraying speed, the shortest coating time, and the water vapor transmission rate. The results are shown in Table 2.

TABLE 1

| PVA polymer | Average degree of hydrolysis (mol %) | Viscosity of 4% by mass aqueous solution (mPa · s) | Transparency of liquid after addition of 130 mL of 1-propanol (%) [Whether Requirement (A) is satisfied] | Supernatant concentration after addition of 230 mL of 1-propanol (%) [Whether Requirement (B) is satisfied] | Value of Formula (3) based on LC-CAD measurement [Whether Requirement (C) is satisfied] |
|---|---|---|---|---|---|
| Synthesis Example 1 | 88.2 | 5.2 | 18.5 [Yes] | 0.83 [Yes] | 43 [Yes] |
| Synthesis Example 2 | 88.3 | 5.2 | 9.2 [Yes] | 0.85 [Yes] | 51 [Yes] |
| Synthesis Example 3 | 88.3 | 5.3 | 30.0 [Yes] | 0.76 [Yes] | 40 [Yes] |
| Synthesis Example 4 | 88.2 | 5.2 | 7.1 [Yes] | 0.85 [Yes] | 60 [Yes] |
| Synthesis Example 5 | 88.4 | 5.3 | 5.9 [Yes] | 0.87 [Yes] | 70 [Yes] |
| Synthesis Example 6 | 88.5 | 5.4 | 10.3 [Yes] | 0.84 [Yes] | 49 [Yes] |
| Synthesis Example 7 | 88.2 | 5.5 | 35.4 [Yes] | 0.71 [No] | 30 [Yes] |
| Synthesis Example 8 | 88.1 | 5.3 | 99.4 [No] | 0.80 [Yes] | 14 [No] |
| Comparative Synthesis Example 1 | 88.3 | 5.3 | 99.4 [No] | 0.62 [No] | 12 [No] |
| JP-05 | 88.2 | 5.3 | 99.2 [No] | 0.68 [No] | 13 [No] |

TABLE 2

| | | Coating test | | Water vapor transmission rate of film of coating composition (g/m² · day) |
|---|---|---|---|---|
| | PVA polymer | Maximum spraying speed (g/min) | 3% by mass coating time (min) | |
| Example 1 | Synthesis Example 1 | 4.85 | 52 | 32 |
| Example 2 | Synthesis Example 2 | 5.19 | 48 | 31 |
| Example 3 | Synthesis Example 3 | 3.79 | 66 | 30 |
| Example 4 | Synthesis Example 4 | 5.32 | 47 | 32 |
| Example 5 | Synthesis Example 5 | 5.53 | 45 | 33 |
| Example 6 | Synthesis Example 6 | 5.15 | 49 | 31 |
| Example 7 | Synthesis Example 7 | 4.17 | 60 | 33 |
| Example 8 | Synthesis Example 8 | 3.91 | 64 | 32 |

TABLE 2-continued

|  | PVA polymer | Coating test | | Water vapor transmission rate of film of coating composition (g/m² · day) |
|---|---|---|---|---|
|  |  | Maximum spraying speed (g/min) | 3% by mass coating time (min) |  |
| Comparative Example 1 | Comparative Synthesis Example 1 | 2.69 | 93 | 33 |
| Comparative Example 2 | JP-05 | 2.27 | 110 | 32 |
| Comparative Example 3 | JP-05/ PEG6000 | 4.40 | 57 | 52 |

Table 2 clearly shows that by using the PVA polymers of Synthesis Examples 1 to 8 used in Examples 1 to 7, each of which polymers had a wide distribution of the degree of hydrolysis and satisfied the requirement (A) and/or the requirement (B), the spraying speed was increased and the predetermined amount of film coating on tablets was achieved in a shorter time as compared to Comparative Examples 1 and 2. Such a high speed spraying means less likelihood of sticking between tablets or sticking between tablets and the pan. That is, it was confirmed that the film coating composition of the present invention is less likely to cause sticking between tablets or sticking between tablets and the pan when used for coating or tablets.

Also, the films formed of the coating compositions of Examples 1 to 8 each had a low water vapor transmission rate as with the case of a conventional PVA. The water vapor transmission rate was lower than that of the film formed of the coating composition containing PVA and the plasticizer, i.e. the film of Comparative Example 3, where the plasticizer was used for the purpose of improving the productivity. For the reasons described above, the use of the film coating composition of the present invention enables rapid production of tablets having highly moistureproofing coating formed thereon.

INDUSTRIAL APPLICABILITY

The film coating composition according to the present invention is characterized in that the composition can be used for pharmaceutical formulations in Japan, the US, and Europe, that even when the composition is used for coating of tablets without any substance other than PVAs, the tablets do not tend to stick to each other and thereby the coating time can be shortened, and that the composition can form a coating film having an excellent moistureproofing property and a high water solubility. Therefore, producing a solid oral formulation using the film coating composition of the present invention is extremely useful in the industrial field.

The invention claimed is:

1. A film coating composition for a solid oral formulation, the composition comprising a polyvinyl alcohol polymer having an average degree of hydrolysis of 85.0 to 89.0 mol % measured according to JIS K6726 and satisfying a requirement that a 4% by mass aqueous solution of the polyvinyl alcohol polymer has a viscosity of from 3.0 mPa·s to 5.5 mPa·s as measured according to JIS K6726,
wherein the polyvinyl alcohol polymer further satisfies the following requirement (A) or (B):
Requirement (A): the transparency of a liquid obtainable by adding 130.0 mL of 1-propanol to 100.0 g of a 5.0% by mass aqueous solution of the polyvinyl alcohol polymer followed by stirring is 50.0% or less at 20° C., or
Requirement (B): a supernatant obtainable by adding 230.0 mL of 1-propanol to 100.0 g of a 5.0% by mass aqueous solution of the polyvinyl alcohol polymer followed by stirring and subsequent 24-hour standing at 20° C. has a concentration of 0.75% by mass or more.

2. A solid oral formulation, which is a tablet comprising a medicinal substance and coated with the film coating composition according to claim 1.

3. A method for producing a solid oral formulation, comprising applying or spraying an aqueous solution and/or a water-based solution comprising the film coating composition according to claim 1 onto a tablet comprising a medicinal substance to coat the surface of the tablet with the film coating composition.

4. A film coating composition for a solid oral formulation, the composition comprising a polyvinyl alcohol polymer having an average degree of hydrolysis of 85.0 to 89.0 mol % measured according to JIS K6726 and satisfying a requirement that a 4% by mass aqueous solution of the polyvinyl alcohol polymer has a viscosity of from 3.0 mPa·s to 5.5 mPa·s as measured according to JIS K6726,
wherein the polyvinyl alcohol polymer further satisfies the following requirement (C):
Requirement (C): when the polyvinyl alcohol polymer is subjected to liquid chromatography using a charged aerosol detector and a column, wherein the column has the following features: Carbon load: 8%, Maximum pressure: 4500 psi, Particle diameter: 3 µm, Pore diameter: 300 Å, Stationary phase: C18, Surface area: 100 m²/g, Length: 150 mm, Diameter: 4.6 mm, pH: 2.5 to 7.5, and Material: Glass Lined Tubing, under the measurement conditions shown below and when a detected intensity after baseline correction at a retention time $T_i$ [min] is expressed as $P_i$ [pA], $T_n$ and $T_w$, which are represented by Formulae (1) and (2), respectively, using $T_i$ and $P_i$, satisfy Formula (3) provided that measurement data are obtained from 5.0 to 12.0 minutes of retention time with a data sampling period of 500 milliseconds;
Measurement conditions:
Concentration of aqueous solution of polyvinyl alcohol polymer: 0.1% by mass
Volume of injected aqueous solution of polyvinyl alcohol polymer: 2 µL
Column temperature: 50° C.
Flow rate: 1.0 mL/min
Eluent: Mixed solvent of water and methanol
Gradient conditions of eluent: the mixing ratio of water and methanol in the eluent is changed at a constant rate from 95:5 to 15:85 during measurement time of 0 to 10 minutes, and is kept constant at 15:85 during measurement time of 10 to 15 minutes;
Formulae:

$$T_n = \Sigma(T_i \times P_i)/\Sigma(P_i) \qquad \text{Formula (1)}$$

$$T_w = \Sigma(T_i^2 \times P_i)/\Sigma(T_i \times P_i) \qquad \text{Formula (2)}$$

$$\{(T_w/T_n)-1\} \times 1000 > 20 \qquad \text{Formula (3)}.$$

5. A solid oral formulation, which is a tablet comprising a medicinal substance and coated with the film coating composition according to claim 4.

6. A method for producing a solid oral formulation, comprising applying or spraying an aqueous solution and/or a water-based solution comprising the film coating composition according to claim 4 onto a tablet comprising a medicinal substance to coat the surface of the tablet with the film coating composition.

7. A film coating composition for a solid oral formulation, the composition comprising a polyvinyl alcohol polymer having an average degree of hydrolysis of 85.0 to 89.0 mol % measured according to JIS K6726 and satisfying a requirement that a 4% by mass aqueous solution of the polyvinyl alcohol polymer has a viscosity of from 3.0 mPa·s to 5.5 mPa·s as measured according to JIS K6726, wherein the polyvinyl alcohol polymer further satisfies the following requirements (A) and (B):

Requirement (A): the transparency of a liquid obtainable by adding 130.0 mL of 1-propanol to 100.0 g of a 5.0% by mass aqueous solution of the polyvinyl alcohol polymer followed by stirring is 50.0% or less at 20° C., and Requirement (B): a supernatant obtainable by adding 230.0 mL of 1-propanol to 100.0 g of a 5.0% by mass aqueous solution of the polyvinyl alcohol polymer followed by stirring and subsequent 24-hour standing at 20° C. has a concentration of 0.75% by mass or more.

8. A solid oral formulation, which is a tablet comprising a medicinal substance and coated with the film coating composition according to claim 7.

9. A method for producing a solid oral formulation, comprising applying or spraying an aqueous solution and/or a water-based solution comprising the film coating composition according to claim 7 onto a tablet comprising a medicinal substance to coat the surface of the tablet with the film coating composition.

* * * * *